United States Patent
Koseoglu et al.

(10) Patent No.: US 12,428,372 B2
(45) Date of Patent: Sep. 30, 2025

(54) ODSO ACID MEDIUM, ODSO ACID MIXTURE MEDIUM, AND USES THEREOF

(71) Applicant: Saudi Arabian Oil Company, Dhahran (SA)

(72) Inventors: Omer Refa Koseoglu, Dhahran (SA); Robert P. Hodgkins, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/720,702

(22) Filed: Apr. 14, 2022

(65) Prior Publication Data

US 2023/0331668 A1   Oct. 19, 2023

(51) Int. Cl.
*C07C 321/12*    (2006.01)
*C10G 17/02*    (2006.01)

(52) U.S. Cl.
CPC ............ *C07C 321/12* (2013.01); *C10G 17/02* (2013.01); *C10G 2300/202* (2013.01)

(58) Field of Classification Search
CPC .................................................. C07C 321/12
See application file for complete search history.

(56) References Cited

U.S. PATENT DOCUMENTS

| | | | | |
|---|---|---|---|---|
| 2,433,396 A | * | 12/1947 | Proell | C07C 303/22 562/118 |
| 2,727,920 A | * | 12/1955 | Johnson | C07C 303/16 562/118 |
| 3,420,797 A | | 1/1969 | Ishida et al. | |
| 4,238,551 A | * | 12/1980 | Lal | C23F 13/005 428/670 |
| 5,011,983 A | | 4/1991 | Behr | |
| 5,591,237 A | * | 1/1997 | Bell | C10L 1/10 44/325 |
| 9,204,996 B2 | | 12/2015 | Till et al. | |
| 9,271,947 B2 | | 3/2016 | Lechado et al. | |
| 9,670,299 B2 | | 6/2017 | Luo | |
| 10,124,056 B2 | | 11/2018 | Milner et al. | |
| 10,399,934 B2 | | 9/2019 | Fonfe et al. | |

(Continued)

FOREIGN PATENT DOCUMENTS

| | | |
|---|---|---|
| EP | 1493768 A1 | 1/2005 |
| GB | 1313813 A | 4/1973 |

(Continued)

OTHER PUBLICATIONS

International Search Report and Written opinion for corresponding International Patent Application No. PCT/US2023/018424 dated Jun. 30, 2023. 7 pages.

*Primary Examiner* — Ellen M Mcavoy
*Assistant Examiner* — Ming Cheung Po
(74) *Attorney, Agent, or Firm* — Leason Ellis LLP

(57) ABSTRACT

An acid medium is provided comprising one or more water-soluble oxidized disulfide oil ODSO compounds. The use of such an acid medium is disclosed as a replacement for conventional acids. Embodiments of the present disclosure are directed to an ODSO acid or ODSO acid mixture medium comprising, consisting of or consisting essentially of one or more polar water-soluble ODSO compounds, including polar water-soluble ODSO compounds present in an effluent refinery hydrocarbon stream recovered following catalytic oxidation of mercaptans present in a petroleum feedstream.

19 Claims, 3 Drawing Sheets

(56) References Cited

U.S. PATENT DOCUMENTS

| | | | |
|---|---|---|---|
| 10,781,168 B2 * | 9/2020 | Koseoglu | C07C 315/02 |
| 10,793,782 B2 | 10/2020 | Koseoglu et al. | |
| 10,807,947 B2 * | 10/2020 | Koseoglu | C07C 315/02 |
| 10,927,318 B2 * | 2/2021 | Koseoglu | C10L 1/2431 |
| 11,111,212 B2 * | 9/2021 | Koseoglu | C07C 317/04 |
| 11,649,405 B1 * | 5/2023 | Hodgkins | C10G 53/14 |
| | | | 208/252 |
| 2013/0079402 A1 | 3/2013 | Bravo et al. | |
| 2013/0143730 A1 | 6/2013 | Fraga-Dubreuil et al. | |
| 2015/0238579 A1 | 8/2015 | Arjona et al. | |
| 2017/0114001 A1 | 4/2017 | Atkins et al. | |
| 2020/0181073 A1 | 6/2020 | Koseoglu et al. | |
| 2020/0181074 A1 | 6/2020 | Koseoglu et al. | |

FOREIGN PATENT DOCUMENTS

| | | |
|---|---|---|
| JP | 5000301 B2 | 8/2012 |
| WO | 2021182958 A1 | 9/2021 |

* cited by examiner

ODSO ACID MEDIUM, ODSO ACID MIXTURE MEDIUM, AND USES THEREOF

FIELD OF THE DISCLOSURE

The present disclosure relates to an acid medium and uses thereof.

BACKGROUND OF THE DISCLOSURE

In general, acids can be described using the Brønsted-Lowry or Lewis theories. Brønsted-Lowry acids are molecules that are capable of donating a proton to another substance, and contain a hydrogen atom bonded to a chemical structure that is still energetically favorable after loss of hydrogen ion. An aqueous solution of an acid has a pH less than 7 and is colloquially also referred to as "acid". On the pH scale, lower values correspond to higher acidity and thus a higher concentration of positive hydrogen ions in the solution. Common acids are hydrochloric (HCl), hydrofluoric (HF), sulfuric ($H_2SO_4$) and nitric ($HNO_3$) acids. A Lewis acid is the one that forms a covalent bond with an electron pair in the molecule structure. Examples are aluminum chloride ($AlCl_3$), boron trifluoride ($BF_3$).

Acids are commonly used in countless chemical, petrochemical, industrial, and petroleum refining processes. As noted above, typical acids include hydrochloric, hydrofluoric acid, sulfuric acid and nitric acid. It would be desirable to provide a replacement for these conventional acids, particularly using compounds derived from a stream that is otherwise considered an undesirable by-product.

Within a typical refinery, there are by-product streams that must be treated or otherwise disposed of. The mercaptan oxidation process, commonly referred to as the MEROX process, has long been employed for the removal of the generally foul smelling mercaptans found in many hydrocarbon streams and was introduced in the refining industry over fifty years ago. Because of regulatory requirements for the reduction of the sulfur content of fuels for environmental reasons, refineries have been, and continue to be faced with the disposal of large volumes of sulfur-containing by-products. Disulfide oil (DSO) compounds are produced as a by-product of the MEROX process in which the mercaptans are removed from any of a variety of petroleum streams including liquefied petroleum gas, naphtha, and other hydrocarbon fractions. It is commonly referred to as a 'sweetening process' because it removes the sour or foul smelling mercaptans present in crude petroleum. The term "DSO" is used for convenience in this description and in the claims, and will be understood to include the mixture of disulfide oils produced as by-products of the mercaptan oxidation process. Examples of DSO include dimethyldisulfide, diethyldisulfide, and methylethyldisulfide.

The by-product DSO compounds produced by the MEROX unit can be processed and/or disposed of during the operation of various other refinery units. For example, DSO can be added to the fuel oil pool at the expense of a resulting higher sulfur content of the pool. DSO can be processed in a hydrotreating/hydrocracking unit at the expense of higher hydrogen consumption. DSO also has an unpleasant foul or sour smell, which is somewhat less prevalent because of its relatively lower vapor pressure at ambient temperature; however, problems exist in the handling of this oil.

Commonly owned U.S. Pat. No. 10,807,947 which is incorporated by reference herein in its entirety discloses a controlled catalytic oxidation of MEROX process by-products DSO. The resulting oxidized material is referred to as oxidized disulfide oil (ODSO). As disclosed in 10,807,947, the by-product DSO compounds from the mercaptan oxidation process can be oxidized, in the presence of a catalyst. The oxidation reaction products constitute an abundant source of ODSO compounds, sulfoxides, sulfonates, sulfinates and sulfones.

The ODSO stream so-produced contains ODSO compounds as disclosed in U.S. Pat. Nos. 10,781,168 and 11,111,212 as compositions (such as a solvent), in U.S. Pat. No. 10,793,782 as an aromatics extraction solvent, and in U.S. Pat. No. 10,927,318 as a lubricity additive, all of which are incorporated by reference herein in their entireties. In the event that a refiner has produced or has on hand an amount of DSO compounds that is in excess of foreseeable needs for these or other uses, the refiner may wish to dispose of the DSO compounds in order to clear a storage vessel and/or eliminate the product from inventory for tax reasons.

Thus, there is a clear and long-standing need to provide an efficient and economical process for the treatment of the large volumes of DSO by-products and their derivatives to effect and modify their properties in order to facilitate and simplify their environmentally acceptable disposal, and to utilize the modified products in an economically and environmentally friendly manner, and thereby enhance the value of this class of by-products to the refiner.

In regard to the above background information, the present disclosure is directed to provide a technical solution for an effective substance used as a replacement for conventional acids in various chemical, petrochemical, industrial, and petroleum refining processes.

SUMMARY OF THE DISCLOSURE

In certain embodiments, an acid medium is provided. The acid medium comprises one or more water-soluble oxidized disulfide oil (ODSO) compounds.

In certain embodiments, the one or more ODSO compounds are water-soluble ODSO compounds having 3 or more oxygen atoms and include one or more compounds selected from the group consisting of (R—SOO—SO—R'), (R—SOO—SOO—R'), (R—SO—SOO—OH), (R—SOO—SOO—OH), (R—SOO—SO—OH), (R'—SO—SO—OR), (R'—SOO—SO—OR), (R'—SO—SOO—OR) and (R'—SOO—SOO—OR), wherein R and R' can be the same or different C1-C10 alkyl or C6-C10 aryl. In certain embodiments, the one or more ODSO compounds are water-soluble ODSO compounds having 3 or more oxygen atoms and include a mixture of two or more compounds selected from the group consisting of (R—SOO—SO—R'), (R—SOO—SOO—R'), (R—SO—SOO—OH), (R—SOO—SOO—OH), (R—SOO—SO—OH), (R'—SO—SO—OR), (R'—SOO—SO—OR), (R'—SO—SOO—OR) and (R'—SOO—SOO—OR), wherein R and R' can be the same or different C1-C10 alkyl or C6-C10 aryl. In certain embodiments, the one or more ODSO compounds are water-soluble ODSO compounds having 3 or more oxygen atoms and include one or more compounds selected from the group consisting of (R—SOO—SO—R'), (R—SOO—SOO—R'), (R—SO—SOO—OH), (R—SOO—SOO—OH), (R—SO—SO—OH), (R—SOO—SO—OH), wherein R and R' are the same or different C1-C10 alkyl or C6-C10 aryl. In certain embodiments, the one or more ODSO compounds are water-soluble ODSO compounds having 3 or more oxygen atoms and include a mixture of two or more compounds selected from the group consisting of (R—SOO—SO—R'), (R—SOO—SOO—R'), (R—SO—SOO—OH), (R—SOO—SOO—

OH), (R—SO—SO—OH), (R—SOO—SO—OH), wherein R and R' are the same or different C1-C10 alkyl or C6-C10 aryl. In certain embodiments, a mixture of ODSO compounds corresponds to oxidized disulfide oils present in an effluent refinery hydrocarbon stream recovered following catalytic oxidation of mercaptans present in the effluent refinery hydrocarbon stream.

In certain embodiments, the acid medium is provided in an aqueous solution. In certain embodiments, the acid medium as in any of the foregoing embodiments further comprising one or more additional acidic components, for example, hydrochloric acid, hydrobromic acid, hydrofluoric acid, phosphoric acid, sulfuric acid, nitric acid, aqua regia, citric acid or acetic acid.

In certain embodiments, a method of using the acid medium is provided comprising incorporating the acid medium in a solution, wherein the acid medium acidifies the solution or wherein the acid medium neutralizes the solution. In certain embodiments the acid medium has a pH less than about 7, 4 or 1.

In certain embodiments, the method includes synthesis of mesoporous silica, wherein the solution comprises at least a silica source, an optional organosilane and a surfactant as a soft template material to influence a silica mesoporous structure precursors for the synthesis of mesoporous silica. In certain embodiments, the method includes synthesis of AlPO or SAPO materials, wherein the solution comprises precursors for the synthesis of AlPO or SAPO materials.

In certain embodiments, a method of using the acid medium is provided comprising contacting a solid material with the acid medium. In certain embodiments, the acid medium is brought into contact for etching the solid material. In certain embodiments, the acid medium is brought into contact for peptizing the solid material. In certain embodiments, the solid material contains aluminum and wherein the acid medium is brought into contact for dealuminating the solid material.

In certain embodiments, a method of using the acid medium is provided comprising: introducing a hydrocarbon feedstream into an alkylation unit in the presence of the acid medium, and maintaining the hydrocarbon feedstream in contact with the acid medium in the alkylation unit for a time and under predetermined conditions to produce an alkylated product. For example, the hydrocarbon feedstream can be derived from one or more unit operations such as an FCC unit, a delayed coking unit, a fluid coking unit, a visbreaking unit, a thermal cracking unit, a pyrolysis unit or a stream cracking unit. In certain embodiments the hydrocarbon feedstream is derived from a single hydrocarbon cracking unit operation that is rich in C5 to C14 olefins and aromatics boiling in the range of from 15° C. to 250° C. In certain embodiments alkylation occurs at a temperature in the range of from 25-250 C and a pressure in the range of from 1-30 bar.

Any combinations of the various embodiments and implementations disclosed herein can be used. These and other aspects and features can be appreciated from the following description of certain embodiments and the accompanying drawings and claims.

BRIEF DESCRIPTION OF THE DRAWINGS

The process of the disclosure will be described in more detail below and with reference to the attached drawings in which the same number is used for the same or similar elements.

DETAILED DESCRIPTION OF CERTAIN EMBODIMENTS OF THE DISCLOSURE

Figures 1, 2:
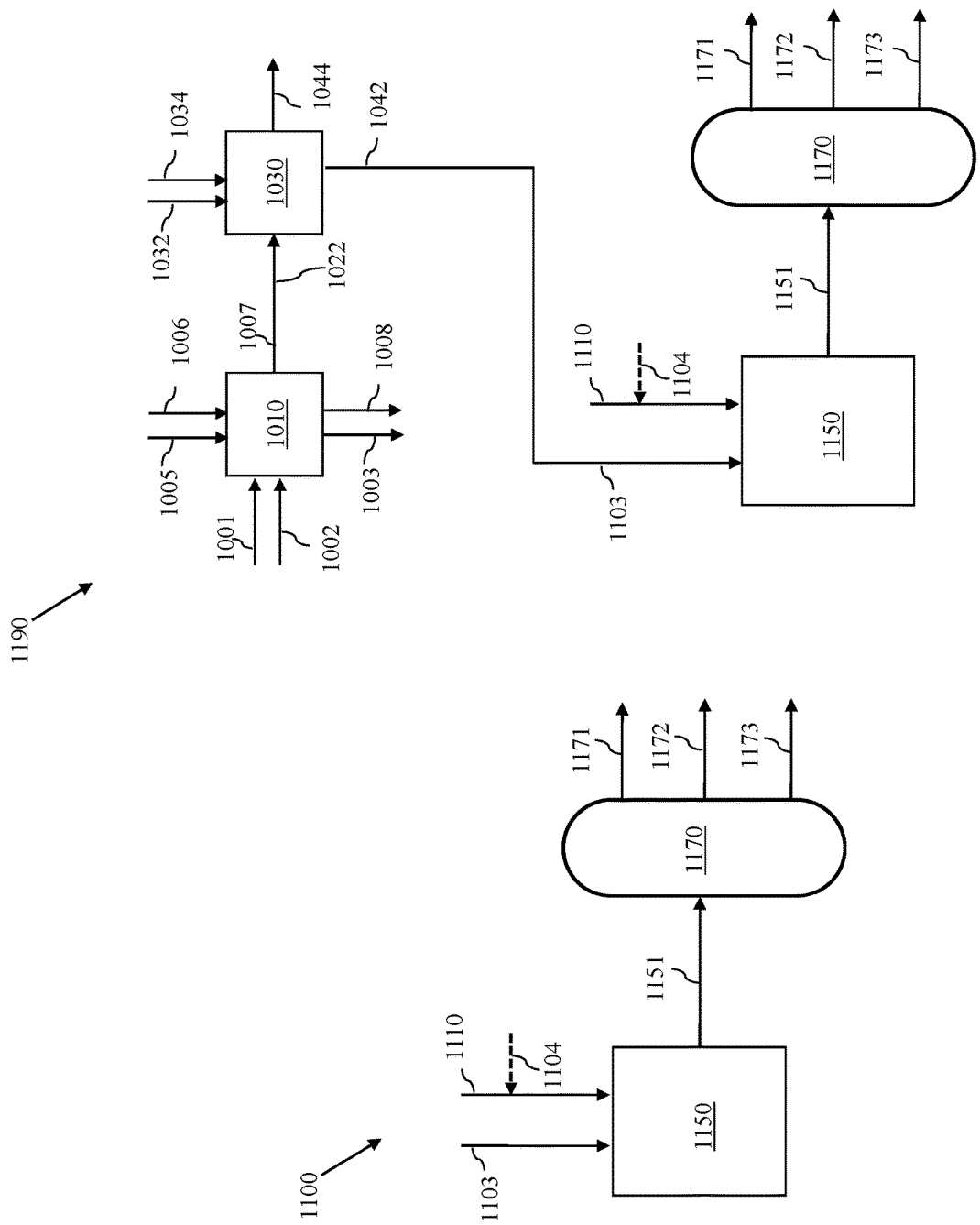
FIG. 1 is a simplified process flow diagram of an alkylation process in accordance with this disclosure.
FIG. 2 is a simplified process flow diagram of an alkylation process integrated with a MEROX/E-MEROX process in accordance with this disclosure.

Example embodiments of the present disclosure are directed to one or more ODSO compounds that are used as acids. The ODSO acid or ODSO acid mixture has a pH of less than 7, less than or equal to 4, or less than or equal to 1. The acid can be a mixture that comprises two or more ODSO compounds. In the description herein, the terms "oxidized disulfide oil", "ODSO", "ODSO mixture" and "ODSO compound(s)" may be used interchangeably for convenience. As used herein, the abbreviations of oxidized disulfide oils ("ODSO") and disulfide oils ("DSO") will be understood to refer to the singular and plural forms, which may also appear as "DSO compounds" and "ODSO compounds," and each form may be used interchangeably. In certain instances, a singular ODSO compound may also be referenced.

Embodiments of the present disclosure are directed to an ODSO acid or ODSO acid mixture medium comprising, consisting of or consisting essentially of one or more polar water-soluble ODSO compounds, including polar water-soluble ODSO compounds present in an effluent refinery hydrocarbon stream recovered following catalytic oxidation of mercaptans present in a petroleum feedstream.

In an embodiment, an ODSO acid or ODSO acid mixture is incorporated in a solution. For example, the components of the solution in the absence of the acid medium can be characterized by an "original pH" that is reduced to a "modified pH." In certain embodiments the solution is aqueous. In certain embodiments the ODSO acid or ODSO acid mixture acidifies the solution to a modified pH of less or equal to 7, and less than the original pH. In certain embodiments in which the pH of the solution is greater than 7, the ODSO acid or ODSO acid mixture neutralizes the solution to a modified pH of less than the original pH.

In certain embodiments, an acid medium is provided that is undiluted from controlled catalytic oxidation of DSO, and includes about 50-100, 75-100, 90-100 percent by mass of one or more ODSO compounds, or an ODSO mixture (referred to herein for convenience as a "neat" ODSO acid medium). In certain embodiments, an acid medium comprises a neat ODSO acid medium that is diluted with water, for instance wherein the neat ODSO acid medium comprises 0.1-99.9, 1-99.9, 5-99.9, 10-99.9, 25-99.9, 50-99.9, 0.1-90, 1-90, 5-90, 10-90, 25-90, 50-90, 0.1-75, 1-75, 5-75, 10-75, 25-75 or 50-75 percent by mass of the overall solution of acid medium. In certain embodiments, an acid medium comprises a neat ODSO acid medium or a diluted ODSO acid medium, mixed with one or more additional acidic components, for example hydrochloric acid, hydrobromic acid, hydrofluoric acid, phosphoric acid, sulfuric acid, nitric acid, aqua regia (a mixture of nitric acid and hydrochloric acid, optimally in a molar ratio of nitric:hydrochloric of 1:3), citric acid or acetic acid. The additional acid is in aqueous diluted form, for example from a solution of 0.1-99.9 percent by mass, which is combined with the neat or diluted ODSO. In certain embodiments, an acid medium comprises a diluted ODSO acid medium, mixed with one or more additional acidic components (including those listed above); the additional acidic component(s) can be provided in pure (100 percent by mass acid) or in aqueous diluted form, for example from a solution of 0.1-99.9 percent by mass; the pure or diluted acid is combined with the diluted ODSO acid medium to form an acid medium herein.

In an embodiment, an ODSO acid or ODSO acid mixture is brought into contact with a substance such as a solid material for treatment to modify one or more properties. In an embodiment, an ODSO acid or ODSO acid mixture is brought into contact with a solid material for etching the solid material. In an embodiment, an ODSO acid or ODSO acid mixture is brought into contact with a solid material for peptizing the solid material. In an embodiment, an ODSO acid or ODSO acid mixture is brought into contact with a solid material for dealuminating the solid material.

In an embodiment, an ODSO acid or ODSO acid mixture is a used as an acid component in the synthesis of mesoporous silica. In typical production of mesoporous silica, a homogeneous aqueous mixture is formed of effective amounts of at least an acid, a silica source and a surfactant as a soft template material to influence a silica mesoporous structure. A conventional acid medium is typically hydrochloric acid (HCl), sulfuric acid ($H_2SO_4$), hydrobromic acid (HBr), phosphoric acid ($H_3PO_4$) or nitric acid ($HNO_3$), which is used in an effective amount to attain a pH level less than about 3, 2 or 1. In certain embodiments of a process herein, an amount of the conventional acid medium is supplemented or substituted with an effective amount ODSO acid or an ODSO acid mixture to produce mesoporous silica. The homogeneous aqueous mixture is heated under conditions and for a time effective to form a precipitate suspended in a supernatant, wherein the time and conditions are effective to realize mesoporous silica as the precipitate, which is recovered, for example by filtration, washing and drying. An example of such a process is disclosed in co-pending and commonly owned U.S. patent application Ser. No. 17/347,125 filed on Jun. 14, 2021, entitled "Method For Manufacture Of Mesoporous Silica In The Presence Of Water-Soluble ODSO," which is incorporated by reference herein in its entirety.

In an embodiment, an ODSO acid or ODSO acid mixture is an acid component in the synthesis of silicoaluminophosphate (SAPO) or aluminophosphate (AlPO). In typical production of SAPO, a homogeneous aqueous mixture is formed of effective amounts of at least an acid and precursors, the precursors including a silica source, an alumina source and a phosphorus source; in production of AlPO, a homogeneous aqueous mixture is formed of effective amounts of at least an acid and precursors, the precursors including an alumina source and a phosphorus source, and optionally a silica source. The conventional acid medium is typically hydrochloric acid (HCl), sulfuric acid ($H_2SO_4$), hydrobromic acid (HBr), phosphoric acid ($H_3PO_4$) or nitric acid ($HNO_3$), which is used in an effective amount to attain a pH level less than about 10, for example in the range of about 3-10, 3-9, 3-8, 4-10, 4-9, or 4-8. In certain embodiments of a process herein, an amount of the conventional acid medium is supplemented or substituted with an effective amount ODSO acid or an ODSO acid mixture, to produce SAPO or AlPO. The homogeneous aqueous mixture is heated under conditions and for a time effective to form a precipitate suspended in a supernatant, wherein the time and conditions are effective to realize SAPO and/or AlPO as the precipitate, which is recovered, for example by filtration, washing and drying.

In an embodiment, an ODSO acid or ODSO acid mixture is brought into contact with a solid material, such as an inorganic oxide material, to impart properties so that the treated material acts as a binder material used in catalyst manufacturing. In conventional catalyst manufacturing including use of an inorganic oxide binder, treatment of the material with an acid medium increases efficacy and catalyst quality. An amount of the conventional acid medium is substituted with an effective amount ODSO acid or an ODSO acid mixture to treat the inorganic oxide material. An example of such a process is peptizing as disclosed in co-pending and commonly owned U.S. patent application Ser. No. 17/689,009 filed on Mar. 8, 2022 entitled "Peptization Agent And Solid Catalyst Manufacturing Method," which is incorporated by reference herein in its entirety.

In an embodiment, an ODSO acid or ODSO acid mixture is brought into contact with a zeolite material used in catalyst manufacturing, for instance for dealumination. In conventional catalyst manufacturing including use of zeolites, treatment with an acid medium increases efficacy and catalyst quality in one or more process steps. An amount of the conventional acid medium is substituted with an effective amount ODSO acid or an ODSO acid mixture to treat the inorganic oxide material.

In embodiments depicted in FIGS. 1 and 2, an ODSO acid or ODSO acid mixture is used in a process where a hydrocarbon feedstream is introduced into an alkylation unit in the presence of at least one catalyst and maintained in contact with the catalyst for a time and under predetermined conditions to produce an alkylated product.

Referring to FIG. 1, the embodiment of the process of the present disclosure will be described for increasing middle distillate production from an olefinic heavy naphtha stream containing aromatics and olefins by the catalytic conversion to alkyl aromatics in the diesel boiling point range. In some embodiments, the olefins in the olefinic heavy naphtha stream comprises olefine with carbon numbers in the range of from 5 to 14. The integrated alkylation process and system for its practice is referred to generally as 1100. Feedstream 1110 enters alkylation unit 1150 where it contacts an ODSO acid or ODSO acid mixture 1103 for a time that is sufficient to complete the alkylation of the aromatic compounds by the ionic constituents that formed from the dissociation of the olefinic compounds present in the mixed feedstream. For example, the ODSO acid or ODSO acid mixture functions as a catalyst to protonate alkenes such as propene and butene to produce reactive carbocations such as alkylate isobutane. An alkylated product stream 1151 is recovered and passed to a fractionation zone 1170 where gasoline and middle distillates are separated and recovered as product streams 1171 and 1172, respectively, and a bottoms stream 1173 is discharged from the fractionation zone 1170. The fractionation zone 1170 can include fractionation units such as flash vessels, fractionation columns, gas stripping, steam stripping, vapor-liquid separators, distillation columns, or a combination of these units. An optional excess molar quantity of hydrogen 1104 is mixed with the feedstream 1110 upstream of the alkylation unit 1150.

In an embodiment depicted in FIG. 2, an ODSO acid or ODSO acid mixture is used in a process where a hydrocarbon feedstream is introduced into an alkylation unit in the presence of at least one catalyst and maintained in contact with the catalyst for a time and under predetermined conditions to produce an alkylated product. The ODSO acid or ODSO acid mixture can be derived from an effluent refinery hydrocarbon stream recovered from a MEROX unit 1010 and an E-MEROX unit 1030, that operate similarly to the MEROX and E-MEROX units in FIGS. 3 and 4, with similar references numbers representing similar units/feeds. The ODSO compounds 1042 from the E-MEROX unit 1030 is the ODSO acid catalyst 1103 used in the alkylation reaction. The alkylation process and system integrated with the MEROX/E-MEROX units is referred to generally as 1190.

In some embodiments, the alkylation reaction can be conducted at a temperature in the range of from about 25° C. to less than 250° C. In some embodiments, the alkylation reaction is conducted at a temperature in the range of from about 25° C. to 90° C. In certain embodiments, the alkylation reaction is conducted at a pressure in the range of from about 1 bar to 30 bar.

In certain embodiments, the olefins concentration in the feed can range from 1 W % to 60 W %. In some embodiments, the W % of the olefins concentration in the feed is in the range of from 30-46, 30-59, 30-9, 39-46, 39-59, 39-9, 6-46, 6-59 or, 6-9 W %. In certain embodiments, the aromatic concentration in the feed is in the range of from 1 W % to 60 W %. In some embodiments, the aromatic W % of the concentration in the feed is in the range of from 13-19, 13-16, 13-37, 10-19, 10-16, 10-37, 25-19, 25-16, or 25-37 W %. The feedstream 1110 can be derived from any suitable unit operation that is conveniently available within the battery limits of the refinery. For example, the source of the feedstream can be an FCC unit, a thermal cracking unit, or a combination thereof. The types of thermal cracking unit operations from which suitable olefin streams are derived are delayed or fluid coking units, visbreaking units, thermal cracking units, pyrolysis units, steam cracking units, and other cracking processes that do not employ hydrogen. As will be apparent to one of ordinary skill in the art, not all of these unit operations are likely to be found within a single refinery. The hydrocarbon feedstream 1110 comprises aromatic and olefinic compounds. In some embodiments, an aromatics containing feedstream and an olefinic feedstream are combined upstream (not shown) to produce the hydrocarbon feedstream 1110. In other embodiments, hydrocarbon feedstream 1110 is derived from a single source that contains both aromatic and olefinic compounds within the same stream. In some embodiments, the hydrocarbon feedstream 1110 is derived from a single hydrocarbon cracking unit operation that is rich in $C_5$ to $C_{14}$ olefins and aromatics boiling in the range of from 15° C. to 250° C.

In the process herein, an effective amount of one or more ODSO compounds are used as an acid component, that is, as a pH modifier and/or as a substitute or replacement for conventional acids. The effective amount is dependent on the use of the acid. For example, the effective amount of ODSO can be that which is suitable to achieve similar pH levels as the conventional acid medium being replaced. For example, in some embodiments, the acid is a Brønsted-Lowry acid, and the effective amount of ODSO is that which is donates an equivalent quantity of protons as the conventional acid medium being replaced.

In certain embodiments, the ODSO compounds used as the ODSO acid or ODSO acid mixture are obtained from controlled catalytic oxidation of disulfide oils from mercaptan oxidation processes. The effluents from controlled catalytic oxidation of disulfide oils from mercaptan oxidation processes includes ODSO compounds and in certain embodiments DSO compounds that were unconverted in the oxidation process. In certain embodiments this effluent contains water-soluble compounds and water-insoluble compounds. The effluent contains at least one ODSO compound, or a mixture of two or more ODSO compounds, selected from the group consisting of compounds having the general formula (R—SO—S—R'), (R—SOO—S—R'), (R—SOO—SO—R'), (R—SOO—SOO—R'), (R—SO—SO—R'), (R—SO—SOO—OH), (R—SOO—SOO—OH), (R—SO—SO—OH), (R—SOO—SO—OH), (R'—SO—SO—OR), (R'—SOO—SO—OR), (R'—SO—SOO—OR) and (R'—SOO—SOO—OR). In certain embodiments, in the above formulae R and R' are the same or different C1-C10 alkyl or C6-C10 aryl. It will be understood that since the source of the DSO is a refinery feedstream, the R and R' substituents vary, e.g., methyl and ethyl subgroups, and the number of sulfur atoms, S, in the as-received feedstream to oxidation can extend to 3, for example, trisulfide compounds.

In certain embodiments the water-soluble compounds and water-insoluble compounds are separated from one another, and the ODSO acid or ODSO acid mixture comprise all or a portion of the water-soluble compounds separated from the total effluents from oxidation of disulfide oils from mercaptan oxidation processes. For example, the different phases can be separated by decantation or partitioning with a separating funnel, separation drum, by decantation, or any other known apparatus or process for separating two immiscible phases from one another. In certain embodiments, the water-soluble and water-insoluble components can be separated by distillation as they have different boiling point ranges. It is understood that there will be crossover of the water-soluble and water-insoluble components in each fraction due to solubility of components, typically in the ppmw range (for instance, about 1-10,000, 1-1,000, 1-500 or 1-200 ppmw). In certain embodiments, contaminants from each phase can be removed, for example by stripping or adsorption.

In certain embodiments an ODSO acid or ODSO acid mixture medium comprises, consists of or consists essentially of at least one water-soluble ODSO compound having 3 or more oxygen atoms that is selected from the group consisting of compounds having the general formula (R—SOO—SO—R'), (R—SOO—SOO—R'), (R—SO—SOO—OH), (R—SOO—SOO—OH), (R—SOO—SO—OH), (R'—SO—SO—OR), (R'—SOO—SO—OR), (R'—SO—SOO—OR) and (R'—SOO—SOO—OR). In certain embodiments an ODSO acid or ODSO acid mixture medium comprises, consists of or consists essentially of a mixture or two or more water-soluble ODSO compounds having 3 or more oxygen atoms, that is selected from the group consisting of compounds having the general formula (R—SOO—SO—R'), (R—SOO—SOO—R'), (R—SO—SOO—OH), (R—SOO—SOO—OH), (R—SOO—SO—OH), (R'—SO—SO—OR), (R'—SOO—SO—OR), (R'—SO—SOO—OR) and (R'—SOO—SOO—OR). In certain embodiments an ODSO acid or ODSO acid mixture medium comprises, consists of or consists essentially of ODSO compounds selected from the group consisting of (R—SOO—SO—R'), (R—SOO—SOO—R'), (R—SO—SOO—OH), (R—SOO—SOO—OH), (R—SO—SO—OH), (R—SOO—SO—OH), and mixtures thereof. In certain embodiments, in the above formulae R and R' are the same or different C1-C10 alkyl or C6-C10 aryl. In certain embodiments, the R and R' are methyl and/or ethyl groups. In certain embodiments, the ODSO compound(s) used as an acid have 1 to 20 carbon atoms.

In certain embodiments, an ODSO acid or ODSO acid mixture medium comprises, consists of or consists essentially of ODSO compounds having an average density greater than about 1.0 g/cc. In certain embodiments, an ODSO acid or ODSO acid mixture medium comprises, consists of or consists essentially of ODSO compounds having an average boiling point greater than about 80° C. In certain embodiments, an ODSO acid or ODSO acid mixture medium comprises, consists of or consists essentially of ODSO compounds having a dielectric constant that is less than or equal to 100 at 0° C.

Table 1 includes examples of polar water-soluble ODSO compounds that contain 3 or more oxygen atoms. In certain embodiments the identified ODSO compounds are obtained from a water-soluble fraction of the effluents from oxidation of DSO obtained from MEROX by-products. The ODSO compounds that contain 3 or more oxygen atoms are water-soluble over effectively all concentrations, for instance, with some minor amount of acceptable tolerance for carry over components from the effluent stream and in the water insoluble fraction with 2 oxygen atoms of no more than about 1, 3 or 5 mass percent.

In certain embodiments the ODSO compounds used as acids comprise all or a portion of the ODSO compounds contained in an oxidation effluent stream that derived from controlled catalytic oxidation of MEROX process by-products, DSO compounds, as disclosed in U.S. Pat. Nos. 10,807,947 and 10,781,168 and as incorporated herein by reference above.

In some embodiments, the ODSO compounds used as an acid correspond to oxidized DSO compounds present in an effluent refinery hydrocarbon stream recovered following the catalytic oxidation of mercaptans present in the hydrocarbon stream. In some embodiments, the DSO compounds are oxidized in the presence of a catalyst.

As noted above, the designation "MEROX" originates from the function of the process itself, that is, the conversion of mercaptans by oxidation. The MEROX process in all of its applications is based on the ability of an organometallic catalyst in a basic environment, such as a caustic, to accelerate the oxidation of mercaptans to disulfides at near ambient temperatures and pressures. The overall reaction can be expressed as follows:

where R is a hydrocarbon chain that may be straight, branched, or cyclic, and the chains can be saturated or unsaturated. In most petroleum fractions, there will be a mixture of mercaptans so that the R can have 1, 2, 3 and up to 10 or more carbon atoms in the chain. This variable chain length is indicated by R and R' in the reaction. The reaction is then written:

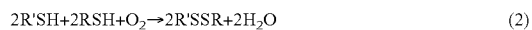

This reaction occurs spontaneously whenever any sour mercaptan-bearing distillate is exposed to atmospheric oxygen, but proceeds at a very slow rate. In addition, the catalyzed reaction (1) set forth above requires the presence of an alkali caustic solution, such as aqueous sodium hydroxide. The mercaptan oxidation proceeds at an economically practical rate at moderate refinery downstream temperatures.

The MEROX process can be conducted on both liquid streams and on combined gaseous and liquid streams. In the case of liquid streams, the mercaptans are converted directly to disulfides which remain in the product so that there is no reduction in total sulfur content of the effluent stream. The MEROX process typically utilizes a fixed bed reactor system for liquid streams and is normally employed with charge stocks having end points above 135° C.-150° C. Mercaptans are converted to disulfides in the fixed bed reactor system over a catalyst, for example, an activated charcoal impregnated with the MEROX reagent, and wetted with caustic solution. Air is injected into the hydrocarbon feedstream ahead of the reactor and in passing through the catalyst-impregnated bed, the mercaptans in the feed are oxidized to disulfides. The disulfides are substantially insoluble in the caustic and remain in the hydrocarbon phase. Post treatment is required to remove undesirable by-products resulting from known side reactions such as the neutralization of $H_2S$, the oxidation of phenolic compounds, entrained caustic, and others.

The vapor pressures of disulfides are relatively low compared to those of mercaptans, so that their presence is much less objectionable from the standpoint of odor; however, they are not environmentally acceptable due to their sulfur content and their disposal can be problematical.

In the case of mixed gas and liquid streams, extraction is applied to both phases of the hydrocarbon streams. The degree of completeness of the mercaptan extraction depends upon the solubility of the mercaptans in the alkaline solution, which is a function of the molecular weight of the individual mercaptans, the extent of the branching of the mercaptan molecules, the concentration of the caustic soda and the temperature of the system. Thereafter, the resulting DSO compounds are separated and the caustic solution is regenerated by oxidation with air in the presence of the catalyst and reused.

Figures 3, 4:
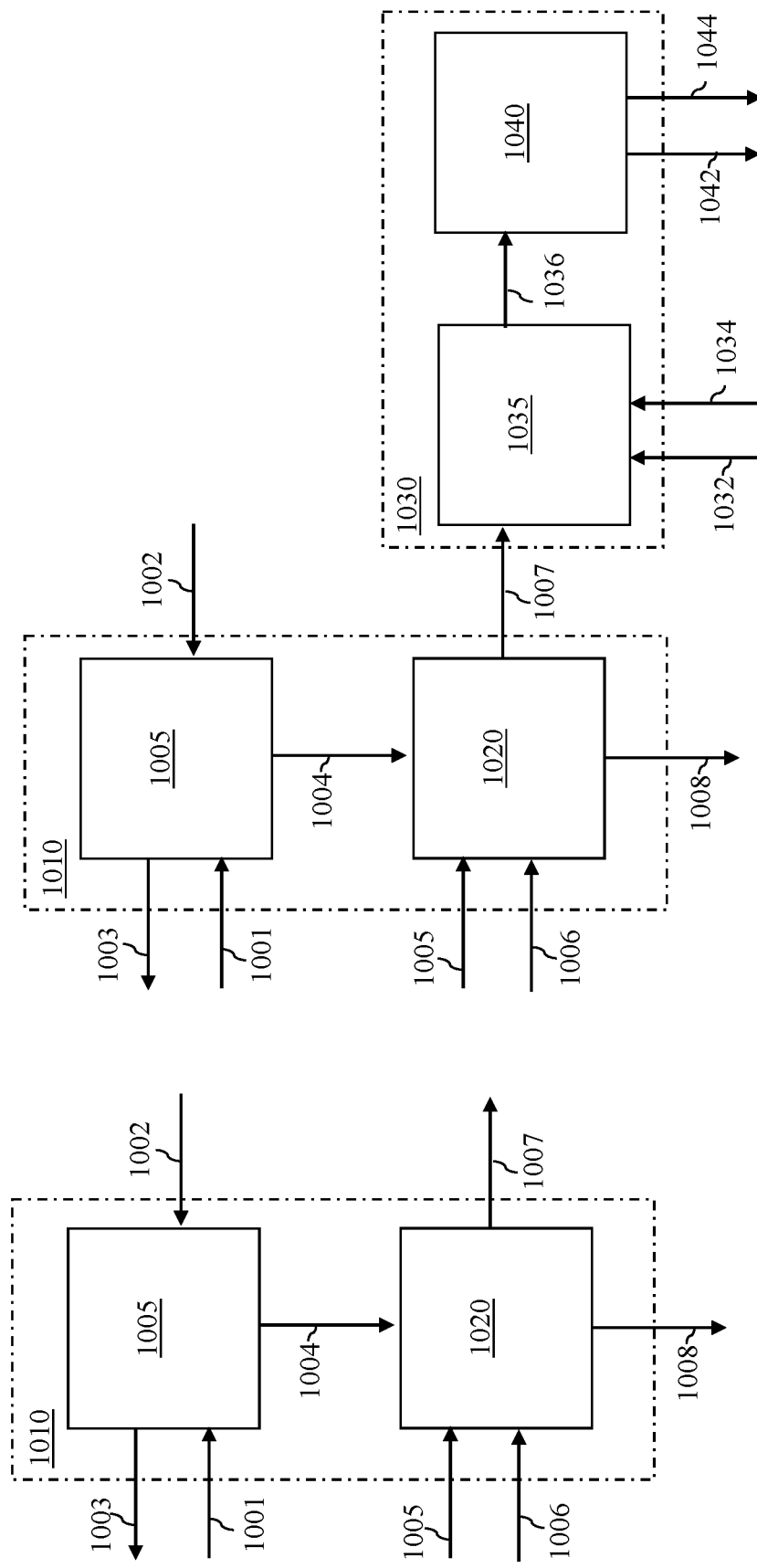
FIG. 3 is a simplified schematic diagram of a generalized version of a conventional mercaptan oxidation or MEROX process for the liquid-liquid extraction of a mercaptan containing hydrocarbon stream.
FIG. 4 is a simplified schematic diagram of a generalized version of an enhanced mercaptan oxidation or E-MEROX process.

FIG. 3 is a simplified schematic of a generalized version of a conventional MEROX process employing liquid-liquid extraction for removing sulfur compounds. A MEROX unit 1010, is provided for treating a mercaptan containing hydrocarbon stream 1001. In some embodiments, the mercaptan containing hydrocarbon stream 1001 is LPG, propane, butane, light naphtha, kerosene, jet fuel, or a mixture thereof. The process generally includes the steps of: introducing the hydrocarbon stream 1001 with a homogeneous catalyst into an extraction vessel 1005 containing a caustic solution 1002, in some embodiments, the catalyst is a homogeneous cobalt-based catalyst; passing the hydrocarbon catalyst stream in counter-current flow through the extraction section of the extraction 1005 vessel in which the extraction section includes one or more liquid-liquid contacting extraction decks or trays (not shown) for the catalyzed reaction with the circulating caustic solution to convert the mercaptans to water-soluble alkali metal alkane thiolate compounds; withdrawing a hydrocarbon product stream 1003 that is free or substantially free of mercaptans from the extraction vessel 1005, for instance, having no more than about 1000, 100, 10 or 1 ppmw mercaptans; recovering a combined spent caustic and alkali metal alkane thiolate stream 1004 from the extraction vessel 1005; subjecting the spent caustic and alkali metal alkane thiolate stream 1004 to catalyzed wet air oxidation in a reactor 1020 into which is introduced catalyst 1005 and air 1006 to provide the regenerated spent caustic 1008 and convert the alkali metal alkane thiolate compounds to disulfide oils; and recovering a by-product stream 1007 of DSO compounds and a minor proportion of other sulfides such as monosulfides and tri-sulfides. The effluents of the wet air oxidation step in the MEROX process can comprise a minor proportion of sulfides and a major proportion of disulfide oils. As is known to those skilled in the art, the composition of this effluent stream depends on the effectiveness of the MEROX process, and sulfides are assumed to be carried-over material. A variety of catalysts have been developed for the commercial practice of the process. The efficiency of the MEROX process is also a function of the amount of $H_2S$ present in the stream. It is a common refinery practice to install a prewashing step for $H_2S$ removal.

An enhanced MEROX process ("E-MEROX") is a modified MEROX process where an additional step is added, in which DSO compounds are oxidized with an oxidant in the presence of a catalyst to produce a mixture of ODSO compounds. The by-product DSO compounds from the mercaptan oxidation process are oxidized, in some embodiments in the presence of a catalyst, and constitute an abundant source of ODSO compounds that are sulfoxides, sulfonates, sulfinates, sulfones and their corresponding di-sulfur mixtures. The disulfide oils having the general formula RSSR' (wherein R and R' can be the same or different and can have 1, 2, 3 and up to 10 or more carbon atoms) can be oxidized without a catalyst or in the presence of one or more catalysts to produce a mixture of ODSO compounds. The oxidant can be a liquid peroxide selected from the group consisting of alkyl hydroperoxides, aryl hydroperoxides, dialkyl peroxides, diaryl peroxides, peresters and hydrogen peroxide. The oxidant can also be a gas, including air, oxygen, ozone and oxides of nitrogen. If a catalyst is used in the oxidation of the disulfide oils having the general formula RSSR' to produce the ODSO compounds, it can be a heterogeneous or homogeneous oxidation catalyst. The oxidation catalyst can be selected from one or more heterogeneous or homogeneous catalyst comprising metals from the IUPAC Group 4-12 of the Periodic Table, including Ti, V, Mn, Co, Fe, Cr, Cu, Zn, W and Mo. The catalyst can be a homogeneous water-soluble compound that is a transition metal containing an active species selected from the group consisting of Mo (VI), W (VI), V (V), Ti (IV), and their combination. In certain embodiments, suitable homogeneous catalysts include molybdenum naphthenate, sodium tungstate, molybdenum hexacarbonyl, tungsten hexacarbonyl, sodium tungstate and vanadium pentoxide. An exemplary catalyst for the controlled catalytic oxidation of MEROX process by-products DSO is sodium tungstate, $Na_2WO_4 \cdot 2H_2O$. In certain embodiments, suitable heterogeneous catalysts include Ti, V, Mn, Co, Fe, Cr, W, Mo, and combinations thereof deposited on a support such as alumina, silica-alumina, silica, natural zeolites, synthetic zeolites, and combinations comprising one or more of the above supports.

The oxidation of DSO typically is carried out in an oxidation vessel selected from one or more of a fixed-bed reactor, an ebullated bed reactor, a slurry bed reactor, a moving bed reactor, a continuous stirred tank reactor, and a tubular reactor. The ODSO compounds produced in the E-MEROX process generally comprise two phases: a water-soluble phase and water-insoluble phase, and can be separated into the aqueous phase containing water-soluble ODSO compounds and a non-aqueous phase containing water-insoluble ODSO compounds. The E-MEROX process can be tuned depending on the desired ratio of water-soluble to water-insoluble compounds presented in the product ODSO mixture. Partial oxidation of DSO compounds results in a higher relative amount of water-insoluble ODSO compounds present in the ODSO product and a near or almost complete oxidation of DSO compounds results in a higher relative amount of water-soluble ODSO present in the ODSO product. Details of the ODSO compositions are discussed in the U.S. Pat. No. 10,781,168, which is incorporated herein by reference above.

FIG. 4 is a simplified schematic of an E-MEROX process that includes E-MEROX unit 1030. The MEROX unit 1010 unit operates similarly as in FIG. 3, with similar references numbers representing similar units/feeds. In FIG. 4, the effluent stream 1007 from the generalized MEROX unit of FIG. 3 is treated. It will be understood that the processing of the mercaptan containing hydrocarbon stream of FIG. 3 is illustrative only and that separate streams of the products, and combined or separate streams of other mixed and longer chain products can be the subject of the process for the recovery and oxidation of DSO to produce ODSO compounds, that is the E-MEROX process. In order to practice the E-MEROX process, apparatus are added to recover the by-product DSO compounds from the MEROX process. In addition, a suitable reactor 1035 add into which the DSO compounds are introduced in the presence of a catalyst 1032 and an oxidant 1034 and subjecting the DSO compounds to a catalytic oxidation step to produce the mixed stream 1036 of water and ODSO compounds. A separation vessel 1040 is provided to separate the by-product 1044 from the ODSO compounds 1042.

The oxidation to produce OSDO can be carried out in a suitable oxidation reaction vessel operating at a pressure in the range from about 1-30, 1-10 or 1-3 bars. The oxidation to produce OSDO can be carried out at a temperature in the range from about 20-300, 20-150, 20-90, 45-300, 15-150 or 45-90° C. The molar feed ratio of oxidizing agent-to-mono-sulfur can be in the range of from about 1:1 to 100:1, 1:1 to 30:1 or 1:1 to 4:1. The residence time in the reaction vessel can be in the range of from about 5-180, 5-90, 5-30, 15-180, 15-90 or 5-30 minutes. In certain embodiments, oxidation of DSO is carried out in an environment without added water as a reagent. The by-products stream 1044 generally comprises wastewater when hydrogen peroxide is used as the oxidant. Alternatively, when other organic peroxides are used as the oxidant, the by-products stream 1044 generally comprises the alcohol of the peroxide used. For example, if butyl peroxide is used as the oxidant, the by-product alcohol 1044 is butanol.

In certain embodiments water-soluble ODSO compounds are passed to a fractionation zone (not shown) for recovery following their separation from the wastewater fraction. The fractionation zone can include a distillation unit. In certain embodiments, the distillation unit can be a flash distillation unit with no theoretical plates in order to obtain distillation cuts with larger overlaps with each other or, alternatively, on other embodiments, the distillation unit can be a flash distillation unit with at least 15 theoretical plates in order to have effective separation between cuts. In certain embodiments, the distillation unit can operate at atmospheric pressure and at a temperature in the range of from 100° C. to 225° C. In other embodiments, the fractionation can be carried out continuously under vacuum conditions. In those embodiments, fractionation occurs at reduced pressures and at their respective boiling temperatures. For example, at 350 mbar and 10 mbar, the temperature ranges are from 80° C. to 194° C. and 11° C. to 98° C., respectively. Following fractionation, the wastewater is sent to the wastewater pool (not shown) for conventional treatment prior to its disposal.

The wastewater by-product fraction can contain a small amount of water-insoluble ODSO compounds, for example, in the range of from 1 ppmw to 10,000 ppmw. The wastewater by-product fraction can contain a small amount of water-soluble ODSO compounds, for example, in the range of from 1 ppmw to 50,000 ppmw, or 100 ppmw to 50,000 ppmw. In embodiments where alcohol is the by-product alcohol, the alcohol can be recovered and sold as a commodity product or added to fuels like gasoline. The alcohol by-product fraction can contain a small amount of water-insoluble ODSO compounds, for example, in the range of from 1 ppmw to 10,000 ppmw. The alcohol by-product fraction can contain a small amount of water-soluble ODSO compounds, for example, in the range of from 100 ppmw to 50,000 ppmw.

EXAMPLE

Figure 5A:
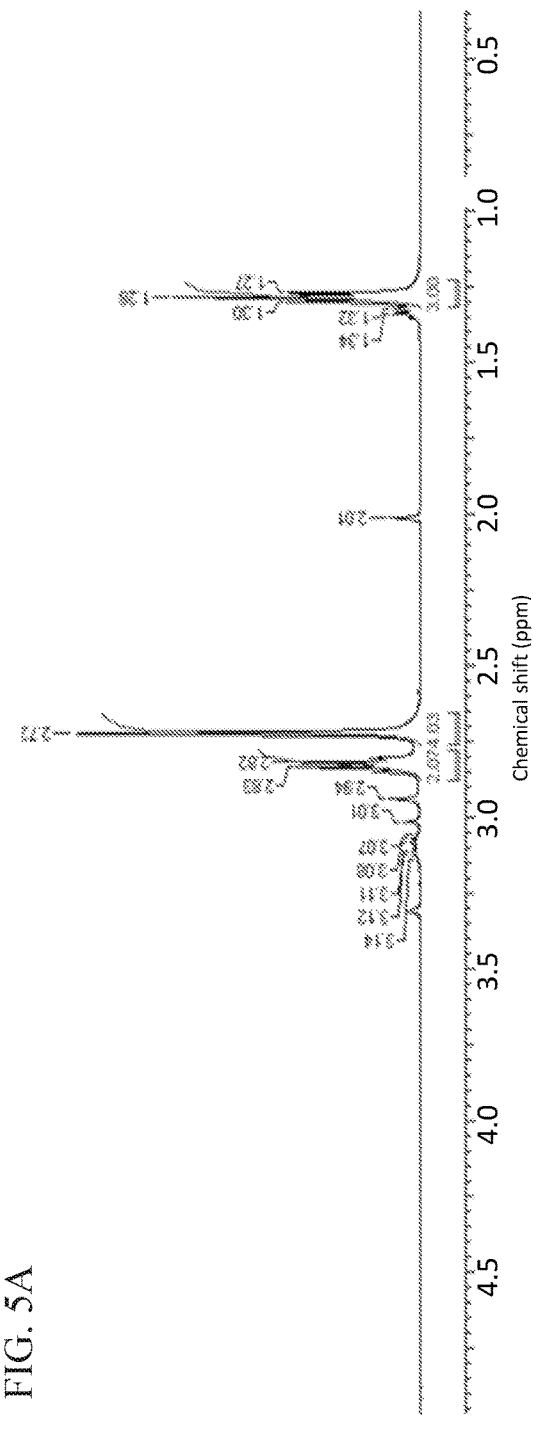
FIG. 5A is the experimental $^1$H-NMR spectrum of the polar, water-soluble ODSO fraction used as an acid medium herein.
Figure 5B:
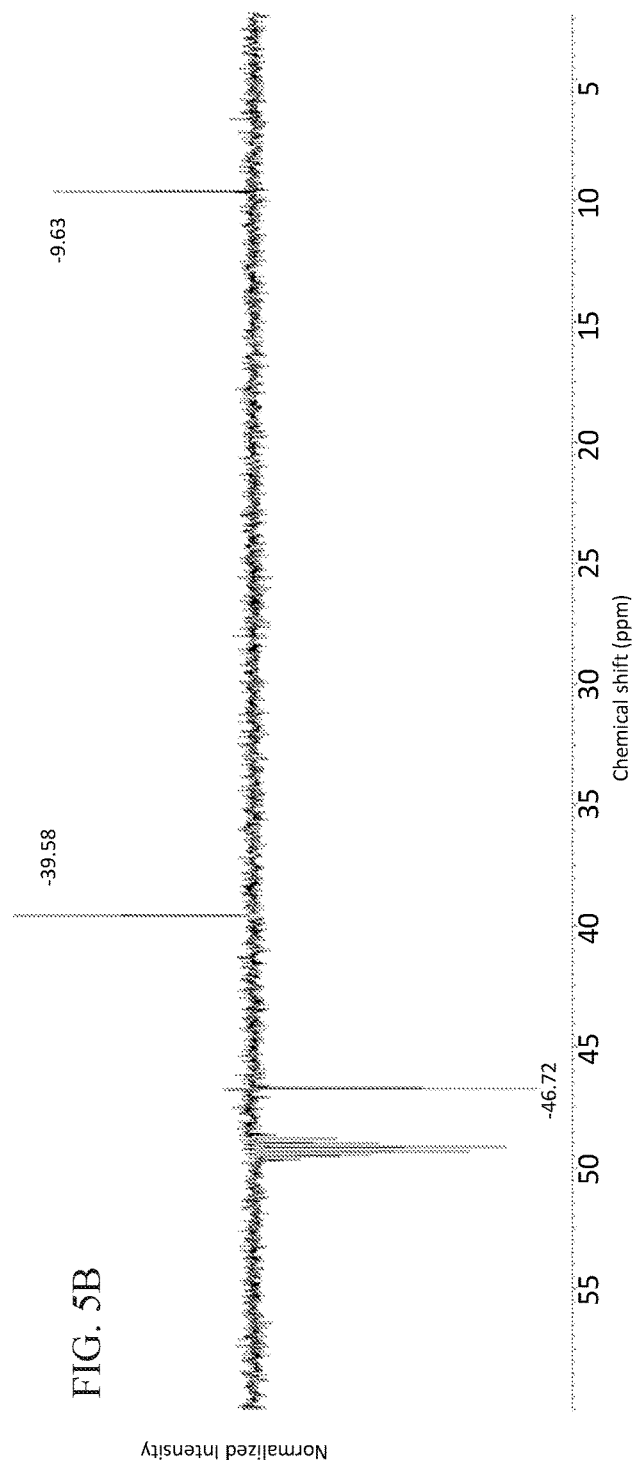
FIG. 5B is the experimental $^{13}$C-DEPT-135-NMR spectrum of the polar, water-soluble ODSO fraction used as an acid medium herein.

Reference Example: The ODSO mixture used in the Example below was produced as disclosed in U.S. Pat. No. 10,781,168, incorporated by reference above, and in particular the fraction referred to therein as Composition 2. Catalytic oxidation a hydrocarbon refinery feedstock having 98 mass percent of C1 and C2 disulfide oils was carried out. The oxidation of the DSO compounds was performed in batch mode under reflux at atmospheric pressure, that is, approximately 1.01 bar. The hydrogen peroxide oxidant was added at room temperature, that is, approximately 23° C. and produced an exothermic reaction. The molar ratio of oxidant-to-DSO compounds (calculated based upon monosulfur content) was 2.90. After the addition of the oxidant was complete, the reaction vessel temperature was set to reflux at 80° C. for approximately one hour after which the water soluble ODSO was produced (referred to as Composition 2 herein and in U.S. Pat. No. 10,781,168) and isolated after the removal of water. The catalyst used in the oxidation of the DSO compounds was sodium tungstate. The Composition 2, referred to herein as "the selected water soluble ODSO fraction," was used. FIG. 5A is the experimental $^1$H-NMR spectrum of the polar, water soluble ODSO mixture that is the selected water soluble ODSO fraction in the example herein. FIG. 5B is the experimental $^{13}$C-DEPT-135-NMR spectrum of the polar, water soluble ODSO mixture that is the selected water soluble ODSO fraction in the example herein. The selected water soluble ODSO fraction was mixed with a CD$_3$OD solvent and the spectrum was taken at 25° C. Methyl carbons have a positive intensity while methylene carbons exhibit a negative intensity. The peaks in the 48-50 ppm region belong to carbon signals of the CD$_3$OD solvent.

When comparing the experimental $^{13}$C-DEPT-135-NMR spectrum of FIG. 5B for the selected water soluble ODSO fraction with a saved database of predicted spectra, it was found that a combination of the predicted alkyl-sulfoxidesulfonate (R—SO—SOO—OH), alkyl-sulfonesulfonate (R—SOO—SOO—OH), alkyl-sulfoxidesulfinate (R—SO—SO—OH) and alkyl-sulfonesulfinate (R—SOO—SO—OH) most closely corresponded to the experimental spectrum. This suggests that alkyl-sulfoxidesulfonate (R—SO—SOO—OH), alkyl-sulfonesulfonate (R—SOO—SOO—OH), alkyl-sulfoxidesulfinate (R—SO—SO—OH) and alkyl-sulfonesulfinate (R—SOO—SO—OH) are major compounds in the selected water soluble ODSO fraction. It is clear from the NMR spectra shown in FIGS. 5A and 5B that the selected water soluble ODSO fraction comprises a mixture of ODSO compounds that form an ODSO acid of the present disclosure.

Example 1

The pH of the selected water soluble ODSO fraction was determined using pH paper produced by VWR International (VWR International, Radnor, PA, USA). The test strip used to test the pH of the ODSO acid aligned closely with the pH reading of 0. This indicates that an aqueous solution of the ODSO acid of the present invention has a pH of approximately 0 or below. This is a similar reading to when a control sample of an aqueous solution of sulfuric acid was tested, not shown.

The methods of using ODSO as an acid component or acid medium, as a substitute for conventional acids described above and characterized in the attached figures are exemplary, and process modifications and variations will be apparent to those of ordinary skill in the art and the scope of protection for the invention is to be defined by the claims that follow.

It is to be understood that like numerals in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms ""including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Notably, the figures and examples above are not meant to limit the scope of the present disclosure to a single implementation, as other implementations are possible by way of interchange of some or all the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

The foregoing description of the specific implementations will so fully reveal the general nature of the disclosure that others can, by applying knowledge within the skill of the relevant art(s), readily modify and/or adapt for various applications such specific implementations, without undue experimentation, without departing from the general concept of the present disclosure. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings accordingly to one example and other dimensions can be used without departing from the disclosure.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

TABLE 1

| ODSO Name | Formula | Structure Examples |
|---|---|---|
| Dialkyl-sulfonesulfoxide Or 1,2-alkyl-alkyl-disulfane 1,1,2-trioxide | (R—SOO—SO—R') | 1,2-Dimethyldisulfane 1,1,2-trioxide |
| Dialkyl-disulfone Or 1,2 alkyl-alkyl-disulfane 1,1,2,2-tetraoxide | (R—SOO—SOO—R') | 1,2-Dimethyldisulfane 1,1,2,2-tetraoxide |
| Alkyl-sulfoxidesulfonate | (R—SO—SOO—OH) | Methylsulfanesulfonic acid oxide |
| Alkyl-sulfonesulfonate | (R—SOO—SOO—OH) | 1-Hydroxy-2-methyldisulfane 1,1,2,2-tetraoxide |
| Alkyl-sulfoxidesulfinate | (R—SO—SO—OH) | 1-Hydroxy-2-methyldisulfane 1,2-dioxide |
| Alkyl-sulfonesulfinate | (R—SOO—SO—OH) | Methylsulfanesulfinic acid dioxide |

R and R' can be the same or different C1-C10 alkyl or C6-C10 aryl.

What is claimed is:

1. An acid medium having a pH of less than about 7 comprising:
    one or more acidic water-soluble oxidized disulfide oil (ODSO) compounds having a pH of less than about 7; and one or more additional acidic components selected from the group consisting of hydrochloric acid, hydrobromic acid, hydrofluoric acid, phosphoric acid, sulfuric acid, nitric acid and aqua regia, wherein the ODSO comprises 25-99.9 percent by mass of the acid medium.

2. The acid medium of claim 1, wherein the one or more ODSO compounds are water-soluble ODSO compounds having 3 or more oxygen atoms and include one or more compounds selected from the group consisting of (R—SOO—SO—R'), (R—SOO—SOO—R'), (R—SO—SOO—OH), (R—SOO—SOO—OH), (R—SOO—SO—OH), (R'—SO—SO—OR), (R'—SOO—SO—OR), (R'—SO—SOO—OR) and (R'—SOO—SOO—OR), wherein R and R' are the same or different C1-C10 alkyl or C6-C10 aryl.

3. The acid medium of claim 1, wherein the one or more ODSO compounds are water-soluble ODSO compounds having 3 or more oxygen atoms and include a mixture of two or more compounds selected from the group consisting of (R—SOO—SO—R'), (R—SOO—SOO—R'), (R—SO—SOO—OH), (R—SOO—SOO—OH), (R—SOO—SO—OH), (R'—SO—SO—OR), (R'—SOO—SO—OR), (R'—SO—SOO—OR) and (R'—SOO—SOO—OR), wherein R and R' are the same or different C1-C10 alkyl or C6-C10 aryl.

4. The acid medium of claim 3, wherein the mixture corresponds to oxidized disulfide oils present in an effluent refinery hydrocarbon stream recovered following catalytic oxidation of mercaptans present in the effluent refinery hydrocarbon stream.

5. The acid medium of claim 1, wherein the one or more ODSO compounds are water-soluble ODSO compounds having 3 or more oxygen atoms and include one or more compounds selected from the group consisting of (R—SOO—SO—R'), (R—SOO—SOO—R'), (R—SO—SOO—OH), (R—SOO—SOO—OH), (R—SO—SO—OH), (R—SOO—SO—OH), wherein R and R' are the same or different C1-C10 alkyl or C6-C10 aryl.

6. The acid medium of claim 5, wherein the mixture corresponds to oxidized disulfide oils present in an effluent refinery hydrocarbon stream recovered following catalytic oxidation of mercaptans present in the effluent refinery hydrocarbon stream.

7. The acid medium of claim 1, wherein the one or more ODSO compounds are water-soluble ODSO compounds having 3 or more oxygen atoms and include a mixture of two or more compounds selected from the group consisting of (R—SOO—SO—R'), (R—SOO—SOO—R'), (R—SO—SOO—OH), (R—SOO—SOO—OH), (R—SO—SO—OH), (R—SOO—SO—OH), wherein R and R' are the same or different C1-C10 alkyl or C6-C10 aryl.

8. The acid medium of claim 7, wherein the mixture corresponds to oxidized disulfide oils present in an effluent refinery hydrocarbon stream recovered following catalytic oxidation of mercaptans present in the effluent refinery hydrocarbon stream.

9. The acid medium as in claim 1 in an aqueous solution.

10. The acid medium of claim 1, wherein the one or more additional acidic components comprises hydrochloric acid.

11. The acid medium of claim 1, wherein the one or more additional acidic components comprises hydrobromic acid.

12. The acid medium of claim 1, wherein the one or more additional acidic components comprises hydrofluoric acid.

13. The acid medium of claim 1, wherein the one or more additional acidic components comprises phosphoric acid.

14. The acid medium of claim 1, wherein the one or more additional acidic components comprises sulfuric acid.

15. The acid medium of claim 1, wherein the one or more additional acidic components comprises nitric acid.

16. The acid medium of claim 1, wherein the one or more additional acidic components comprises aqua regia.

17. The acid medium of claim 1 having a pH of less than about 4.

18. The acid medium of claim 1 having a pH of less than about 1.

19. The acid medium of claim 1, wherein the ODSO comprises 50-99.9 percent by mass of the acid medium.

* * * * *